United States Patent [19]
Falkvall et al.

[11] Patent Number: 5,730,712
[45] Date of Patent: Mar. 24, 1998

[54] EXTRACORPOREAL BLOOD TREATMENT APPARATUS AND METHOD

[75] Inventors: Thore Falkvall, Helsingborg, Sweden; William W. Anderson, Coral Gables, Fla.; Thomas D. Kelly, Portland, Oreg.

[73] Assignee: Althin Medical, Inc., Miami, Fla.

[21] Appl. No.: 374,485

[22] Filed: Jan. 17, 1995

[30] Foreign Application Priority Data

Jan. 17, 1994 [SE] Sweden ................... 9400100

[51] Int. Cl.$^6$ ............... A61M 5/00; B01D 63/02
[52] U.S. Cl. ............... 604/5; 604/4; 210/321.8
[58] Field of Search .............. 604/4–6; 138/40, 138/44, 646, 321.6, 321.8, 321.62, 321.64, 321.67, 321.72, 321.71, 321.88, 321.89

[56] References Cited

U.S. PATENT DOCUMENTS

| | | | |
|---|---|---|---|
| 3,782,382 | 1/1974 | Nattulin et al. | 604/6 |
| 4,568,327 | 2/1986 | Seafert | 604/5 |
| 4,690,245 | 9/1987 | Gregovich et al. | 138/46 |
| 4,861,485 | 8/1989 | Fecondini | 604/5 |
| 4,886,086 | 12/1989 | Etchells et al. | 138/40 |
| 5,008,012 | 4/1991 | Hagihara et al. | 604/6 |
| 5,020,943 | 6/1991 | Filipelli | 138/44 |
| 5,092,836 | 3/1992 | Polaschegg | 604/6 |
| 5,254,249 | 10/1993 | Terada et al. | 604/5 |

Primary Examiner—John G. Weiss
Assistant Examiner—David J. Cho
Attorney, Agent, or Firm—Klarquist Sparkman Campbell Leigh & Whinston, LLP

[57] ABSTRACT

Dialyzers and methods are disclosed for performing shortened extracorporeal blood treatments. A flow restriction is provided in a dialyzer serving to partially impede flow of dialysate through the dialysate compartment of the dialyzer. As a result, the pressure of the dialysate upstream of the flow restriction is sufficient to cause the pressure profile of the dialysate from the dialysate inlet to the dialysate outlet of the dialyzer to be non-linear, in contrast to prior-art dialyzers. This perturbation of the dialysate pressure profile permits a single dialyzer to be used to remove large amounts of blood water from a patient's blood and re-infuse large amounts of liquid to the blood while still attaining a desired net ultrafiltration of the patient without the need for more than one dialyzer per treatment or for a separate replacement fluid.

23 Claims, 3 Drawing Sheets

EXTRACORPOREAL BLOOD TREATMENT APPARATUS AND METHOD

FIELD OF THE INVENTION

The present invention pertains to methods and apparatus used in medical treatment; more specifically to such methods and apparatus for the extracorporeal treatment of blood, and most specifically to such methods and apparatus as used in treatments, such as hemodialysis, hemofiltration, and hemodiafiltration.

BACKGROUND OF THE INVENTION

A number of medical conditions indicate extracorporeal treatment of a patient's blood. Generally, in each of such treatments, blood is withdrawn from the patient, passed extracorporeally through a blood-treatment device, then returned to the patient, usually over a period of time sufficient to treat substantially the entire blood volume of the patient. Well-known methods of extracorporeal blood treatment include hemodialysis, hemofiltration, and hemodiafiltration, each of which has undergone a substantial evolution since inception. Each of these treatments is currently preferably performed using at least one blood-treatment device comprising a casing or housing containing multiple hollow fibers of a semipermeable membrane material. The fibers are bundled together in a manner allowing blood to flow simultaneously and in a parallel manner through the lumina of the fibers while a blood-cleansing liquid is simultaneously passed through the casing so as to bathe the exterior surfaces of the hollow fibers with the liquid.

In the following disclosure, reference is made in the interest of brevity to "dialyzers," but it will be understood that the term "dialyzer" as used herein generally refers not only to hemodialyzers in particular but also to hemofilters, hemodiafilters, and other extracorporeal blood treatment devices employing semipermeable hollow fibers in the general manner discussed above.

During hemodialysis (as a representative example of the foregoing treatments), extracorporeal blood is passed through the lumina of hollow fibers of a dialyzer while a substantially isotonic liquid termed "dialysate" is simultaneously passed through the casing of the dialyzero Solutes and liquid pass between the dialysate and the blood through pores in the semipermeable membrane of the fibers. Factors that govern such passage of solutes and liquid during dialysis include diffusion, convection, and pressure differentials across the semipermeable membrane.

Flow of dialysate and extracorporeal blood through the dialyzer is conventionally performed using a "dialysis machine." Conventional dialysis machines prepare dialysate on-line at the proper concentration and profile of dialysate solutes and at the proper temperature, and provide a number of monitors to ensure patient safety during hemodialysis treatment. Many conventional dialysis machines also deliver dialysate to the dialyzer under careful volumetric control and achieve removal of the desired amount of "blood water" from the patient's blood so as to return the patient's weight to a desirable "dry weight." (As used herein, to "ultrafilter" the patient or the patient's blood means to remove said blood water from the patient or blood, respectively; the blood water actually removed is termed "ultrafiltrate" in the art.)

In the U.S., the real-dollar amount of federal reimbursement per patient per treatment for maintenance hemodialysis has been decreasing for many years. Thus, dialysis clinics in the U.S. have a strong incentive to find ways to shorten the time required for each dialysis treatment. Manufacturers of dialysis machines and dialyzers continually strive to keep pace by increasing the efficiency of dialyzers and designing dialysis machines that provide a more physiologically "profiled" dialysate and a more controlled dialysis treatment.

As used herein, a "conventional hemodialysis treatment" is performed using a "conventional hemodialyzer" and generally requires at least about four hours to complete.

A number of different conventional hemodialyzers are currently available, each having a specific permeability to water and particular blood solutes (having certain molecular weights), depending upon the intended conditions of use. Conventional hemodialyzers usually have a surface area of about 1.0 $m^2$ and are designed to function at blood flow rates of less than about 300 mL/min and exhibit urea clearances below about 200 mL/min. Their permeabilities to blood water are sufficiently low (usually about 6 mL/hr/mmHg or less, in vivo, at a blood flow of 200 mL/min) to permit adequate ultrafiltration control in many instances without having to use a dialysis machine providing volumetrically metered delivery of dialysate to the dialyzer.

As used herein, a "shortened dialysis treatment" is a dialysis treatment normally performed in less than four hours, using a dialyzer specially adapted for such use. Depending upon a number of factors, a shortened dialysis treatment usually cannot be satisfactorily performed using a conventional hemodialyzer.

"Conventional" shortened dialysis treatments are generally performed using dialyzers that, in contrast to conventional hemodialyzers (as defined above), have larger surface areas or substantially increased permeabilities to solutes or blood water, or both. Such dialyzers are termed herein "short-dialysis" (abbreviated "SD") dialyzers. Many SD dialyzers are termed "high-flux" dialyzers, wherein the high "flux" aspect generally refers to the increased permeability of the membrane, compared to conventional hemodialyzers, to blood water and small molecular weight solutes such as urea. Thus, blood water can pass through a unit area of membrane of a high-flux dialyzer at a higher rate per unit pressure than through the same area of membrane of a conventional hemodialyzer. SD dialyzers permit use at higher blood flow rates (e.g., 300–400 mL/min) and dialysate flow rates (e.g., 700–1000 mL/min) than conventional hemodialyzers. Such an elevated flow rate using a high-flux dialyzer allows more blood water to be removed without an excessive increase in blood hematocrit (i.e., without overly hemoconcentrating the blood as the blood flows through the fiber lumina).

Shortened dialysis treatments, unless performed properly, can have adverse clinical consequences. One key concern is not to under-dialyze the patient. That is, the dialysis treatment must achieve adequate removal of waste solutes from the patient's blood so that plasma concentrations of the waste solutes remain at apparently non-toxic levels (i.e., levels at which further reductions in waste solutes will not yield a further decrease in patient morbidity.) Also, the dialysis treatment must not remove blood water at too high a rate or else excessive hypotension of the patient could result. In addition, the extracorporeal blood pressure cannot be elevated to unsafe levels to attain a desired ultrafiltration rate of the patient.

One type of conventional shortened dialysis treatment is termed "high-efficiency dialysis" (abbreviated "HED"). This treatment is generally performed using an SD dialyzer having a somewhat higher urea clearance at elevated blood flow rates compared to a conventional hemodialyzer. The water permeability of the dialyzer used in HED is usually less than about 10 mL/min/mmHg. Blood is passed through the dialyzer at higher than normal blood and dialysate flow rates but at relatively low rates of blood water removal. Although the dialysis machine preferably provides volumetric metering of dialysate delivery to and from the dialyzer and ultrafiltration control, the relatively low water permeability of the dialyzer can permit HED to be performed with manual control of ultrafiltration rate via adjustment of transmembrane pressure (TMP).

Another type of conventional shortened dialysis treatment is termed "high-flux dialysis" (abbreviated "HFD"). This treatment is normally performed using a high-flux dialyzer that has a higher permeability to "middle molecules" (molecules having molecular weights greater than urea, up to that of small proteins) than the high-flux dialyzers used in HED. The dialysis machine must provide volumetric metering of dialysate delivery to and from the dialyzer so as to adequately control ultrafiltration.

Yet another type of conventional shortened dialysis treatment is termed "hemofiltration" (abbreviated "HF"). In HF, extracorporeal blood is passed through a special type of high-flux device termed a "hemofilter" with which large amounts of blood water can be ultrafiltered rapidly (at a filtration rate "$Q_f$") through the membrane as the blood passes through the fiber lumina. In HF, no dialysate is used and no diffusive transfer of solutes from the blood occurs. Rather, bulk flow of blood water (and entrained solutes including "middle molecules") occurs by convection from the blood according to the membrane's sieving coefficient for the water and solutes. A sterile, pyrogen-free, and substantially isotonic "replacement solution" is infused into the blood (normally downstream of the hemofilter) at a rate, relative to $Q_f$, sufficient to achieve a desired ultrafiltration of the patient.

Yet another type of conventional shortened dialysis treatment is termed "hemodiafiltration" (abbreviated "HDF") which is essentially a combination of HFD and HF. Hemodiafiltration is often performed using two high-flux dialyzers connected to each other in series. The first dialyzer generally performs cleansing of the blood by diffusion and aggressive ultrafiltration. The second dialyzer is used to return a desired amount of liquid to the blood (by reverse flux) to counter the excess amount of blood water removed by the first dialyzer and achieve a desired net amount of ultrafiltration of the patient. The liquid returned to the blood is a sterile, pyrogen-free, and substantially isotonic "replacement solution" similar, if not identical, to dialysate. A conventional alternative that eliminates the second dialyzer is to infuse the replacement solution from a container directly into the blood returning to the patient.

Hemodiafiltration offers many of the clinical benefits of HF and HFD with minimal clinical drawbacks. The hemofiltration-derived benefits arise from the solely convective solute transport that occurs during hemofiltration, which provides excellent patient comfort and cardiovascular stability even at rapid rates of ultrafiltration. The high-flux dialysis benefits center on the excellent diffusive transport obtainable during dialysis using a high-flux dialyzer.

Unfortunately, despite the foregoing benefits and the significantly shorter dialysis times achievable using HDF and HF, these treatments are expensive compared to conventional hemodialysis, HED, and HFD. In addition to the cost of a second dialyzer, if used, the increased expense arises, inter alia, from the need to provide a separate replacement fluid. Normally, the replacement fluid is provided in a flexible bag and is very expensive.

Thus, there is a need for a way to reduce the cost of treatments such as HDF and HF to make them more attractive candidates for shortened dialysis treatments. In particular, there is a need for HDF and HF dialyzers that do not require a second dialyzer during use and, most preferably, eliminate the need to provide a separate replacement solution.

SUMMARY OF THE INVENTION

The present invention relates to improved dialyzers and extracorporeal blood treatment methods using said dialyzers, as well as hydraulic circuits comprising the dialyzers.

According to one aspect of the present invention, a dialyzer is provided that comprises a casing having a blood inlet and a blood outlet. The casing also has a dialysate inlet and a dialysate outlet. Preferably, the blood and dialysate inlets and outlets are arranged such that blood and dialysate flow counter-currently through the dialyzer. The dialyzer also comprises a semipermeable membrane normally configured as a parallel array of plural hollow fibers. The fibers extend through the casing and are connected to the blood inlet and outlet so as to conduct extracorporeal blood from the blood inlet through the lumina of the hollow fibers to the blood outlet, while dialysate is conducted from the dialysate inlet through the casing to the dialysate outlet. The dialyzer further includes an impediment serving to restrict the flow of dialysate through the casing in a first region compared to a second region adjacent the first region.

As dialysate passes through the casing of a dialyzer, the flow of dialysate exhibits a pressure profile from the dialysate inlet to the dialysate outlet. In prior-art dialyzers, the pressure profile is substantially linear. In dialyzers according to the present invention, the restriction to dialysate flow in the first region imparted by the impediment serves to increase the dialysate pressure in the first region compared to the second region sufficiently to cause the pressure profile through the casing from the dialysate inlet to the dialysate outlet to be non-linear.

As a result of the non-linear pressure profile, it is now possible to have, for example, ultrafiltration of blood water from the blood to the dialysate in the second region of the dialyzer, and reverse-flux of fluid from the dialysate to the blood in the first region of the dialyzer under all conditions expected to be encountered in an extracorporeal blood treatment employing a dialyzer. Such conditions include situations, such as encountered in hemodiafiltration, in which a large first volume (many liters) of blood water is removed from a patient's blood while liquid must be added back to the blood in an amount that is not only also large but also sized relative to the first volume so as to achieve a desired net ultrafiltration of the patient at the end of the treatment.

Various embodiments of dialyzers according to the present invention are possible in which the impediment has any of the following configurations (not intending to be limiting): (a) an external circumferential annular constriction of the dialyzer casing between the first region and the second region; (b) an internal annular restriction situated inside the casing between the first and second regions; (c) an inclusion body located in the first region; and (d) a reduced size of the casing in the first region that provides the dialysate with a space having a reduced cross-sectional area in which to flow compared to the second region.

The foregoing dialyzers according to the present invention can be adapted for use as hemodialyzers, hemofilters, or hemodiafilters, depending upon any of various factors including, but not limited to, membrane composition, membrane porosity, and membrane surface area in the dialyzer, and other factors.

According to another aspect of the present invention, a dialyzer is provided that comprises a bundle of hollow-fiber membranes disposed longitudinally in a casing. A first inlet and a first outlet are attached to the casing and are connected to the fibers so as to conduct a first liquid, such as extracorporeal blood, through the lumina of the fibers to the first outlet. A second inlet and a second outlet are attached to the casing so as to conduct a second liquid, such as dialysate, through the casing from the second inlet to the second outlet. A flow-restricting means is situated between the second inlet and the second outlet for restricting (i.e., partially impeding) flow of the second liquid through the casing sufficiently to cause the pressure profile of the second liquid, exhibited as the second liquid flows from the second inlet to the second outlet, to be non-linear.

According to a preferred embodiment of the foregoing dialyzer, the bundle of fibers has a first portion and a second portion, and the casing provides a partition between the first and second portions. In this embodiment, the flow-restricting means comprises an opening in the partition through which the second liquid passes while being conducted from the first portion to the second portion of the bundle.

According to another aspect of the present invention, dialysate circuits are provided comprising a dialyzer according to the present invention.

According to yet another aspect of the present invention, methods of performing dialysis are provided. As a first step, an enclosure is provided that is separated by a semipermeable membrane into a first compartment and a second compartment. A first liquid, such as extracorporeal blood, is flowed through the first compartment so as to contact a first surface of the membrane. A second liquid, such as dialysate, is flowed through the second compartment so as to contact a second surface of the membrane opposite the first surface. As the second liquid is flowed through the second compartment, the liquid is maintained at a first pressure over an upstream portion of the second surface, and at a second pressure over a downstream portion of the second surface. The resulting pressure profile of the second liquid as it flows through the second compartment is non-linear. Typically, the first pressure is obtained by restricting flow of the second liquid over the upstream portion relative to the downstream portion. This can be obtained by, e.g., providing a more limited cross-sectional flow area over the first portion through which the second liquid must flow, compared to the second portion.

In the foregoing methods, the upstream portion of the second surface typically experiences a pressure sufficient to cause a convective movement of liquid through the membrane from the second compartment to the first compartment. Conversely, the downstream portion of the second surface experiences a pressure sufficient to cause convective movement of liquid through the membrane from the first compartment to the second compartment. The preferred net result of these two convective movements is a desired net reduction of the volume of the first liquid by ultrafiltration through the membrane from the first compartment to the second compartment.

Consequent to the foregoing features of the present invention, various shortened dialysis procedures are now possible without the need to provide a second dialyzer and/or a separate replacement fluid. In fact, the liquid transferred to extracorporeal blood through the membrane can be the same liquid used to dialyze the blood.

DETAILED DESCRIPTION

The features and advantages of the present invention are more completely understood by considering certain other aspects of the prior art, as follows.

As blood and dialysate flow through a dialyzer, the flows of these liquids experience a certain resistance. As a results dialyzers exhibit a pressure drop (i.e., a lower pressure at an outlet pore relative to the corresponding inlet port) for the blood flow and for the dialysate flow; the magnitudes of the pressure drops can vary substantially from one type of dialyzer to another, and depend in part on the flow rates at which blood and dialysate, respectively, are being urged through the dialyzer.

In addition, in dialyzers through which blood and dialysate flow, diffusion will cause atoms or molecules of certain solutes to pass through the membrane pores from the blood to the dialysate and from the dialysate to the blood. Net movement of a particular solute through the membrane by diffusion occurs as a result, inter alia, of a concentration difference of the solute in the blood relative to the dialysate and vice versa, wherein such movement is from the liquid having a higher concentration of the solute to the liquid having a lower concentration of the solute. Diffusion can occur through the membrane when there is no pressure differential across the membrane and even in the presence of an opposing convective flux through the membrane.

Virtually all the treatments discussed above performed using at least one dialyzer involve removing at least some accumulated liquid (termed herein "blood water") from the patient. Removing blood water from a patient using a dialyzer requires a net flow of liquid (i.e., blood water including dissolved waste solutes) from the blood to the dialysate through pores in the membrane. Basically, in any given portion of the dialyzer, this net flow is effected by maintaining the pressure of the dialysate at a lower level relative to the pressure of the blood, thereby causing convective flow or convection (i.e., flow responsive to a pressure differential) of blood water to the dialysate.

In addition to movement of solutes through the membrane pores via diffusion, as described above, solutes can also be transported through the membrane pores by convection, i.e., the solutes are carried along during bulk flow of liquid through the membrane pores.

Figure 1A:
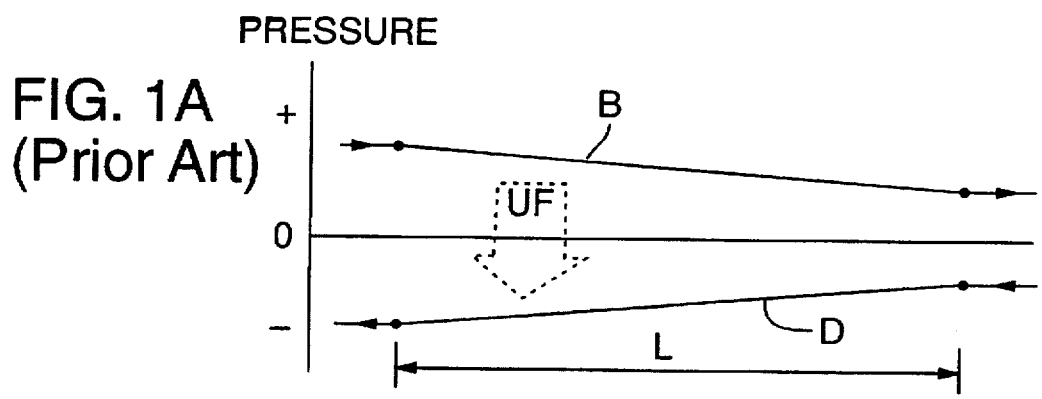
FIG. 1A shows pressure profiles for blood (profile labeled "B") and dialysate (profile labeled "D") flowing counter-currently through a conventional hemodialyzer (shown in FIG. 1B) according to the prior art, showing passage of ultrafiltrate ("UF") from the blood to the dialysate in response to the pressure differential from the blood to the dialysate across the entire length "L" of the dialyzer membrane.
Figure 1B:
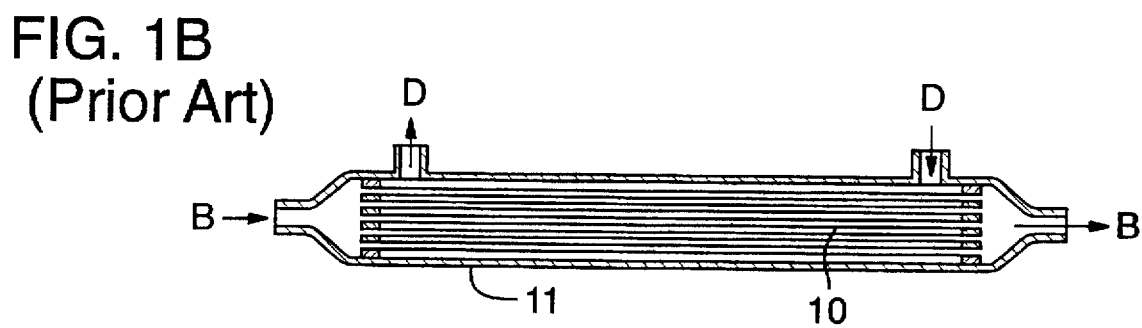
FIG. 1B is a schematic diagram of the hemodialyzer according to the prior art used to produce the profiles shown in FIG. 1A.

An example of convective flow of liquid, for a conventional hemodialyzer used under conventional dialysis conditions, is shown in FIGS. 1A and 1B. In FIG. 1A, the pressure profile for blood ("B") flowing through the lumina of the hollow fibers from left to right (FIG. 1B) is shown above the abscissa (blood usually flows through the dialyzer under positive pressure), and the pressure profile for dialysate ("D") flowing through the dialyzer casing from right to left (FIG. 1B) is shown below the abscissa. The pressure drops over the length L of the dialyzer are illustrated in FIG. 1A by the higher pressures extant at the inlets for blood and dialysate relative to the pressures extant at the outlets for blood and dialysate, respectively. In a conventional hemodialyzer as shown in FIGS. 1A and 1B, the pressure profiles of blood and dialysate are substantially linear over the length L, as would be expected according to principles of fluid mechanics. In FIG. 1A, the blood pressure at any location along the length L is higher than the dialysate pressure. As a result, there is a net flow ("UF") of liquid from the blood to the dialysate along the entire length L.

In a conventional hemodialyzer as shown in FIGS. 1A and 1B, the net mass ("SR"; comprising liquid and certain solutes) transferred from the blood to the dialysate by both convection and diffusion can be expressed as:

$$SR=cL(Df+C)$$

wherein c is a constant; L is the parallel length of the fibers; Df represents mass transported through the membrane by diffusion; and C represents mass transported through the membrane by convection. The (Df+C) term is a sum because, under conditions as shown in FIGS. 1A–1B, both convection and diffusion act in concert to cause a net transfer of mass in the same direction through the membrane (i.e., from blood to dialysate).

Conventional SD dialyzers generally have higher surface areas or substantially increased permeabilities to solutes or water or both. Such dialyzers can provide urea clearances of 225 to 300 mL/min, or higher, at blood flows of 400 mL/min or more. A representative such dialyzer is shown in FIGS. 2A–2B.

Figure 2A:
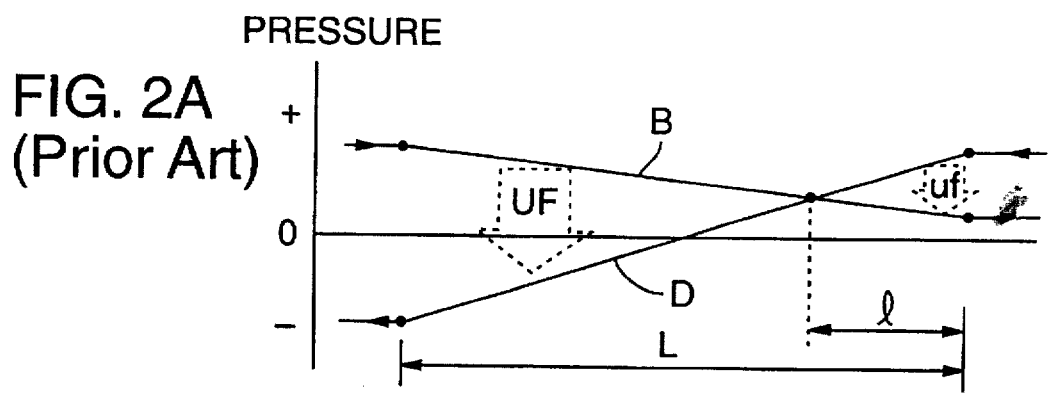
FIG. 2A shows pressure profiles for blood ("B") and dialysate ("D") flowing counter-currently through a conventional hemodialyzer (shown in FIG. 2B) under "high-flow" conditions according to the prior art, showing passage of ultrafiltrate ("UF") from blood to dialysate under conditions in which blood pressure exceeded dialysate pressure, and from dialysate to blood under conditions in which dialysate pressure exceeded blood pressure.
Figure 2B:
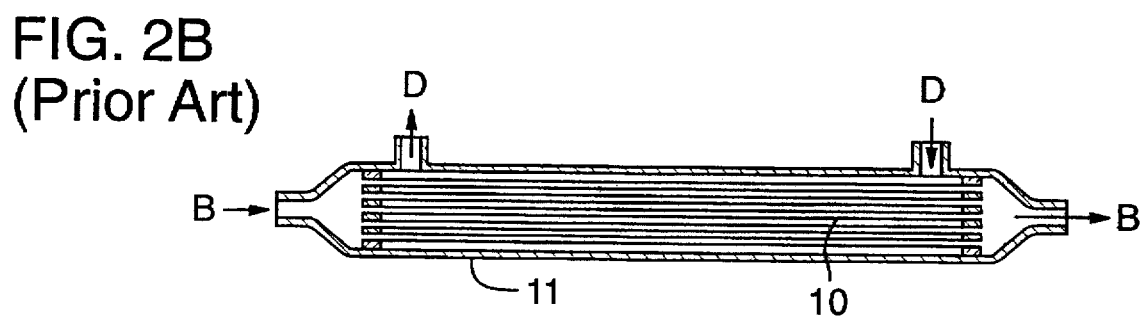
FIG. 2B is a schematic diagram of the hemodialyzer according to the prior art used to produce the profiles shown in FIG. 2A.

Increasing the dialysate flow rate causes the slope of the dialysate pressure profile to increase, which can cause the dialysate pressure profile to cross over the blood pressure profile, as shown in FIG. 2A. Thus, in FIG. 2A, within the portion of fiber length designated "l", the dialysate pressure is greater than the blood pressure (such conditions are referred to in the art as "reverse-TMP" conditions) and there is a net convection of liquid ("uf") through the membrane from the dialysate to the blood. Within the remaining length of fiber (i.e., within L–l), the blood pressure exceeds the dialysate pressure and there is a net convection of liquid ("UF") through the membrane from the blood to the dialysate. So long as "UF" is greater than "uf", there will be a net removal of liquid from the patient.

Referring further to FIG. 2A, the net mass ("SR") removed from the patient is given by:

$$SR=c(L-l)(Df+C)+c(l)(Df-C)$$

wherein L and l are as shown in FIG. 2A; c is a constant; Df represents mass transported through the membrane by diffusion; and C represents mass transported through the membrane by convection. As can be ascertained from this expression, convection and diffusion act together within the region L–l to effect a net movement of mass in the same direction through the membrane. Within the region l, on the other hand, convection urges movement of mass through the membrane in a direction opposite to any mass movement due to diffusion. (Diffusion from the blood to the dialysate can still occur even under the reverse-TMP condition existing in the region l.)

In FIGS. 2A and 2B, the distance "l" depends upon a number of factors including (but not limited to) blood viscosity; number, diameter, and length of the hollow fibers in the dialyzer; the flow rates of blood and dialysate being urged through the dialyzer; the blood pressure; the dialysate pressure; and the desired rate of ultrafiltration of the patient.

In HF and HDF, as discussed above, a large first amount of liquid is removed from the blood, and a second amount of liquid is returned to the blood. In a properly executed HF or HDF treatment, the difference of the first and second amounts generally corresponds to the desired amount of blood water to be removed from the patient to return the patient to her desired "dry weight." In many instances in HF and HDF, the first and second amounts represent many liters.

It has heretofore been impossible in many instances, using a single dialyzer, to remove a very large amount of blood water from the blood, return a large amount of liquid to the blood, and simultaneously achieve a desired net ultrafiltration of the patient. Referring to FIG. 2A, increasing the amount of UF (representing the "first volume") would require raising the blood pressure relative to the dialysate pressure and/or maintaining the blood pressure greater than the dialysate pressure over a greater proportion of the length L. But, manipulating the relative blood and dialysate pressures to maximize UF has an opposite effect on uf (representing the "second volume"). Furthermore, it is unsafe in many instances using the dialyzer of FIGS. 2A–2B to manipulate blood and dialysate pressures sufficiently to place UF and/or uf at desired levels.

The instant invention is directed to dialyzers and methods permitting one to perform the entire spectrum of shortened dialysis treatments, from HED and HFD to HDF and HF, using only a single dialyzer and without the need to provide and administer a separate replacement solution, while still achieving the desired amount of ultrafiltration of the patient.

Figure 3A:
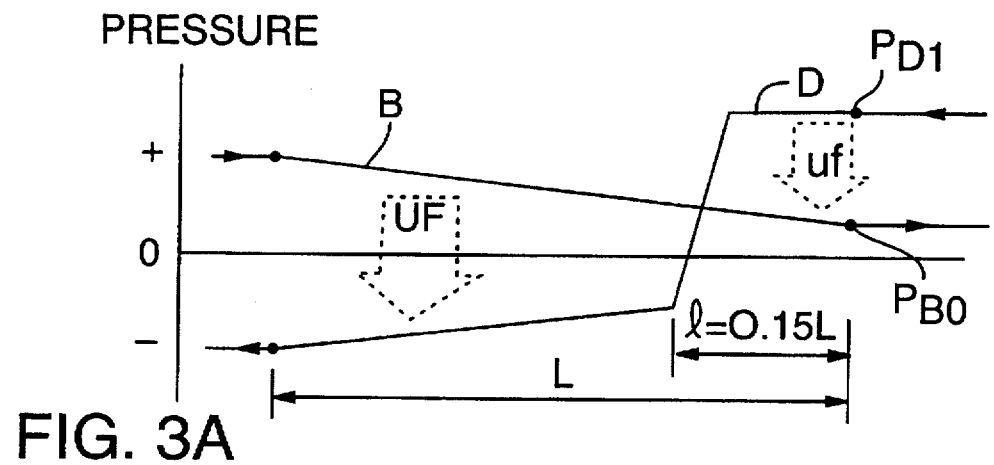
FIG. 3A shows pressure profiles for blood ("B") and dialysate ("D") flowing counter-currently through a hollow-fiber dialyzer according to the present invention (shown in FIG. 3B).
Figure 3B:
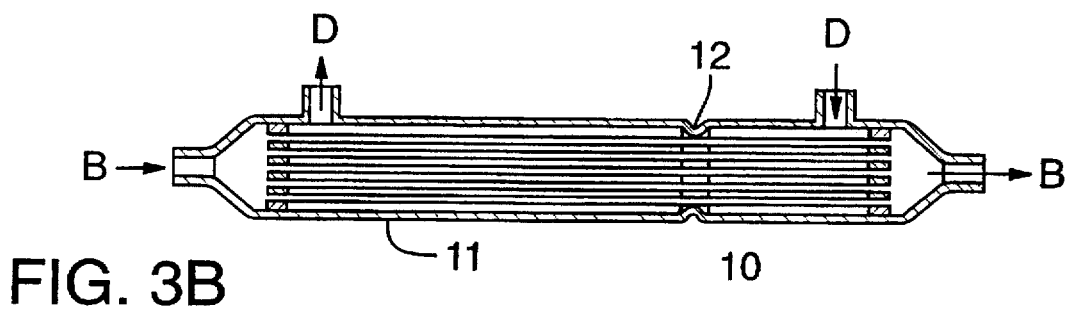
FIG. 3B is a schematic diagram of one embodiment of a hemodialyzer according to the present invention used to produce the profiles shown in FIG. 3A.

FIGS. 3A-3B show a representative embodiment of a dialyzer according to the present invention. Referring first to FIG. 3B, and comparing to FIG. 2B, the dialyzer casing 11 of the FIG.3B dialyzer has a circumferential constriction 12. The constriction 12 impedes the flow of dialysate through the casing sufficiently to cause the pressure of the dialysate flowing through the dialyzer to exhibit a corresponding deviation from linearity, as shown in FIG. 3A. I.e., the dialysate pressure between the constriction 12 and the dialysate inlet of the dialyzer is increased relative to what would be expected from a linear extrapolation of the dialysate pressure profile between the constriction and the dialysate outlet of the dialyzer. The corresponding impact of the increased dialysate pressure on "uf," without any substantial effect on "UF," is immediately apparent in FIG. 3A, compared to FIG. 2A. In FIGS. 2A and 3A, the amounts of "UF" are substantially the same, but the amount of "uf" in FIG. $3a$ is substantially greater than the amount of "uf" in FIG. 2A.

Referring further to FIGS. 3A-3B, the constriction 12 functions as a pressure barrier creating an elevated dialysate pressure within the portion "F" of the length L. Upstream of the constriction 12, the dialysate pressure "D" is greater than the blood pressure "B". Also, immediately upstream of the constriction 12 to the dialysate inlet (the point labeled "$P_{Di}$"), the dialysate pressure has a linear profile, but the slope is not necessarily the same as the slope of the dialysate-pressure profile downstream of the constriction 12. In any event, within the length "l", because the dialysate pressure is greater than the blood pressure, there will be convection of liquid "uf" from the blood to the dialysate. Most of any diffusion performed by the dialyzer will occur within the length (L-l), wherein the mass transferred from the blood to the dialysate is given by the expression:

$$SR=c(L-l)(Df+C)$$

The "second amount" (i.e., the amount represented by "uf" in FIG. 3A) is dictated by the "transmembrane pressure" (abbreviated "TMP") across the membrane 10 within the length "l". The TMP is governed by the relationship:

$$TMP=P_{Di}-P_{BO},$$

wherein $P_{Di}$ is the pressure of the dialysate at the dialysate inlet of the dialyzer; and $P_{BO}$ is the extracorporeal blood pressure at the blood outlet of the dialyzer.

Figure 4:
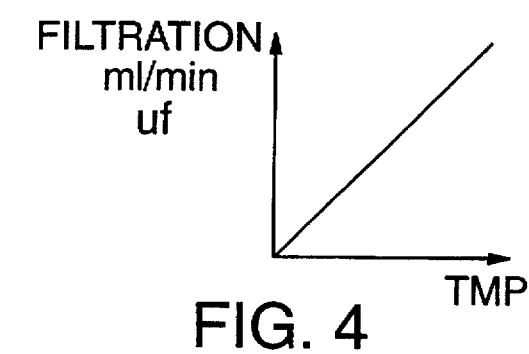
FIG. 4 is a plot showing the relation between ultrafiltration ("uf") and transmembrane pressure ("TMP") in a dialyzer as shown in FIG. 3B.

The relationship of "uf" to TMP is shown in FIG. 4.

Figure 5:
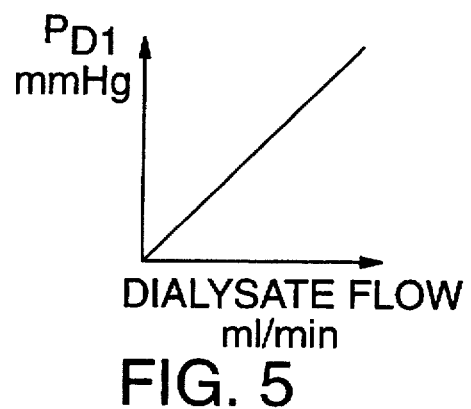
FIG. 5 is a plot showing the relation between dialysate input pressure ("$P_{Di}$") and the flow rate of dialysate in a dialyzer as shown in FIG. 3B.

The relationship of $P_{Di}$ to the flow rate of dialysate through the dialyzer is shown in FIG. 5.

By sensing and monitoring the pressures $P_{Di}$ and $P_{BO}$ using pressure sensors of any of various suitable types known in the art, TMP can be reliably and accurately determined. Using any of various dialyzers according to the present invention, the dialysate and blood flow rates can then be readily adjusted so as to achieve the desired TMP and, thus, the desired "second amount" ("uf").

Several variables concerning the constriction 12 can be manipulated, either alone or in any of various combinations, to achieve a desired "uf" relative to "UF."

One variable is the degree to which the cross-sectional area of the dialysate pathway through the dialyzer is lessened in the vicinity of the constriction. That is, a deep constriction can be provided which causes a profound restriction to dialysate flow, thereby greatly elevating the dialysate pressure upstream of the constriction (i.e., between the constriction and the dialysate inlet) relative to a linear extrapolation of the dialysate pressure downstream of the constriction. Alternatively, the constriction can be relatively slight, causing a slight elevation of upstream dialysate pressure relative to a linear extrapolation of the downstream dialysate pressure.

A second variable is the position of the constriction along the length L. FIG. 3A shows, as an example only and not intended to be limiting in any way, that l=0.15 L. However, depending upon the desired relationship of "uf" to "UF," and upon the desired "first amount" represented by "UF," the constriction 12 can be placed at any of various locations along the length L.

A third variable is the proportion of the length L actually occupied by the constriction 12. I.e., referring to FIG. 3A, the constriction 12 can be highly localized so as to occupy a relatively insignificant proportion of the length L. Alternatively (not shown), the constriction 12 can be much wider so as to occupy a significant proportion of the length L.

Figure 6:
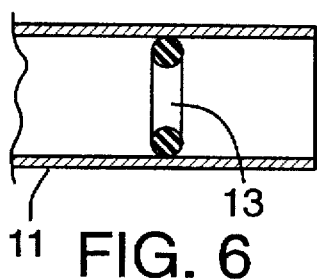
FIGS. 6 to 8 are partial axial cross-sectional views of the casings of alternative embodiments of dialyzers according to the present invention.
Figure 7:
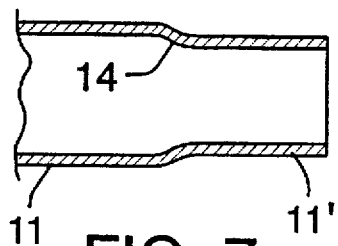
Figure 8:
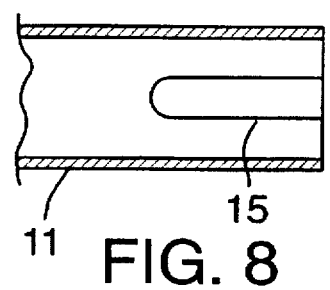

Yet another variable is the shape of the constriction 12. For example, the constriction 12 of FIG. 3A is an external annular depression of the casing 11. FIG. 6 shows an alternative embodiment in which the external annular depression shown in FIG. 3A is replaced with an internal annular restriction 13. (This annular restriction 13 can be made adjustable along the length L.) FIG. 7 shows yet another embodiment in which the casing 11 is provided with a narrower portion 11' and a shoulder 14. In FIG. 7, the narrower portion 11' has a length "l" (FIG. 3A) in which the dialysate pressure is increased relative to a linear extrapolation of the dialysate pressure downstream of the constriction. Also, in FIG. 7, it will be appreciated that the narrower portion 11' has a reduced cross-sectional area through which the dialysate flows, compared to the remaining portion 11 of the casing. FIG. 8 shows yet another alternative embodiment in which the restriction to dialysate flow is imparted by an obstructing occlusion body 15 that reduces the cross-sectional area of the casing 11 over the length "l" through which dialysate can flow.

Figure 9:
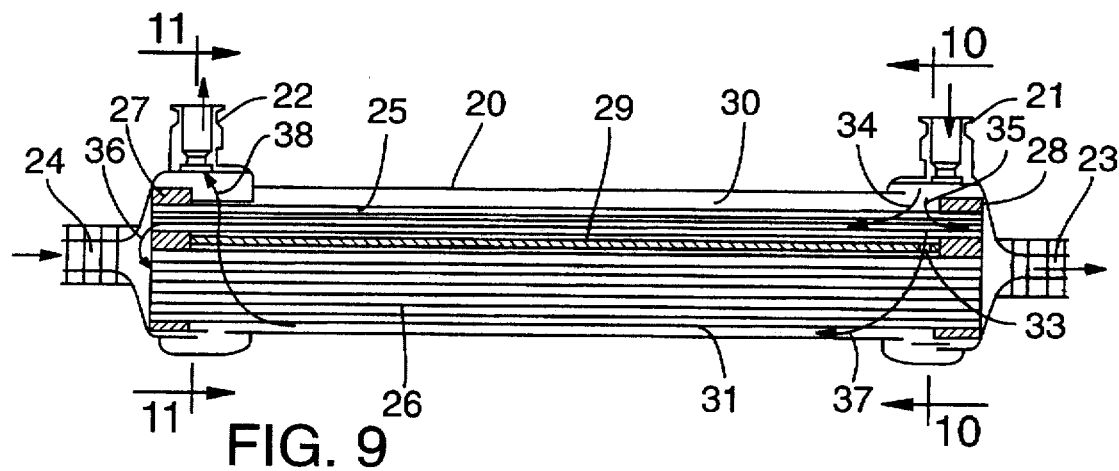
FIG. 9 is a cross-sectional view of yet another alternative embodiment of a dialyzer according to the present invention, the dialyzer having two bundles of hollow fibers each in a separate dialysate compartment, wherein the dialysate compartments are hydraulically connected to each other by a flow restriction in such a way that dialysate flowing through the first compartment has a substantially higher pressure than dialysate flowing through the second compartment.
Figure 11:
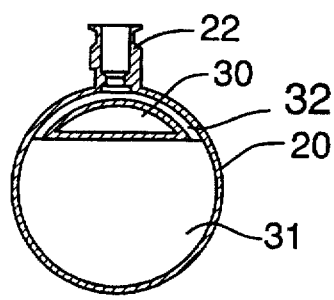
FIGS. 10 and 11 depict cross-sectional views of portions of the embodiment, as indicated in FIG. 9.
Figure 10:
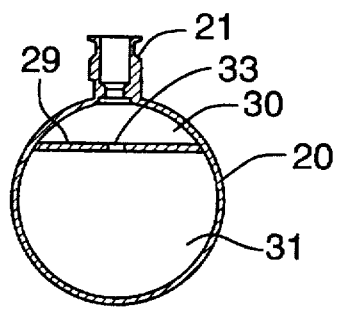

FIGS. 9-11 illustrate yet another alternative embodiment of a dialyzer according to the present invention. Referring first to FIG. 9, a dialyzer is shown comprising a substantially cylindrical casing 20. Provided at opposite ends of the casing 20 are a dialysate inlet 21, and a dialysate outlet 22, both oriented radially relative to the casing 20. Also provided at opposite ends of the casing 20 are a blood outlet 23 and a blood inlet 24, both oriented axially relative to the casing 20. Multiple hollow fibers are provided inside the casing 20, which are divided into a first group 25 and a second group 26. In each of said groups the fibers are arrayed in a parallel manner, and each group is parallel to the other. The ends of the fibers are "potted" relative to the casing 20, as known in the art, forming barriers 27, 28. The barrier 27 forces blood entering the casing through blood inlet 24 to pass through the lumina of the fibers and exit the casing through the blood outlet 28, while forcing dialysate entering the casing through the dialysate inlet 21 to pass through the casing and exit through the dialysate outlet 22. The interior of the casing is substantially divided by a longitudinal partition 29 into a first portion 30 and a second portion 31. The first group 25 of fibers is situated in the first portion 30, and the second group 26 of the fibers is situated in the second portion 31. The first portion 30 communicates with the dialysate inlet 21, and the second portion 31 communicates with the dialysate outlet 22 via passageways 32 extending around the first portion 30 (FIG. 11). The first and second portions 30, 31, respectively, communicate with each other via one or more apertures 33 (FIG. 10) defined by the partition 29. The aperture(s) 33 provide a restricted hydraulic flow of dialysate and thus function in a manner analogous to the constriction 12 shown in FIG. 3B.

The first and second groups 25, 26, respectively, of fibers need not be similar. For example, with respect to the fibers of the first group relative to the fibers of the second group, the following parameters can be the same or different:

(a) lumen diameter;
(b) fiber material;
(c) fiber permeability; and
(d) fiber quantity in each group.

Referring further to the embodiment shown in FIGS. 9–11, dialysate entering the first portion 30 through the dialysate inlet 21 will exhibit an increased pressure in the first portion 30 imparted by restricted dialysate flow through the aperture 33 into the second portion 31. This increased dialysate pressure will normally be higher than the pressure of the blood passing through the fibers in the first group 25. As a result, some dialysate will pass by convection through the pores of the fibers in the first group 25 to the blood passing therethrough (arrows 34, 35 in FIG. 9), thereby adding to the volume of blood in the fibers. Some of the convected dialysate will exit the dialyzer (arrow 35) through the blood outlet 23, and the remainder will pass through the fiber lumina (arrow 34) to be added (arrow 36) to blood entering the dialyzer through the blood inlet 24 so as to enter the lumina of the fibers in the second group 26.

Dialysate passing through the aperture 33 from the first portion 30 to the second portion 31 (arrow 37) then flows through the second portion so as to bathe the exterior surfaces of the fibers in the second group 26. The dialysate flow through the second section 31 is counter-current to the flow of blood through the lumina of the fibers of the second group 26. The dialysate then exits the second portion 31 via the passageway 32 and through the dialysate outlet 22 (arrow 38).

While bathing the fibers of the second group 26, the dialysate will accumulate liquid (ultrafiltrate) that passed through the walls of the fibers in the second group 26 by convection. The amount of ultrafiltrate is controlled so as to include the same amount of liquid that entered the lumina of the fibers of the first group 25 from the dialysate in the first portion 30, plus any desired amount of ultrafiltration of the patient so as to return the patient to her "dry weight."

Figure 12:
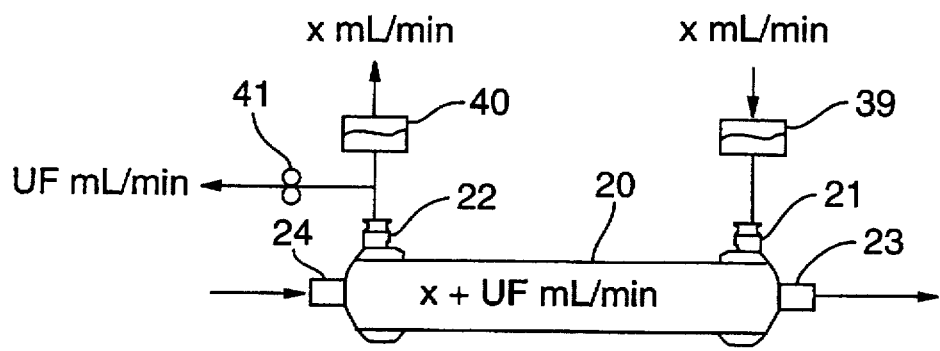
FIG. 12 is a schematic hydraulic diagram of a representative embodiment of a dialysate circuit employing a dialyzer according to the present invention.

When using a dialyzer as shown in FIG. 9, a representative circuit of controlling ultrafiltration is illustrated in FIG. 12, wherein are shown a dialyzer having a casing 20, a dialysate inlet 21, a dialysate outlet 22, a blood inlet 24, and a blood outlet 23. A first volumetric balancing chamber 39 connected to the dialysate inlet 21 provides a pre-set dialysate flow rate (x mL/min) to the dialysate inlet 21. A second volumetric balancing chamber 40 connected to the dialysate outlet 22 provides the same dialysate flow rate (x mL/min) from the dialysate outlet 22. The first and second balancing chambers form a closed hydraulic loop that includes the dialyzer, the line between the first balancing chamber 39 and the dialysate inlet 21, and the line between the second balancing chamber 40 and the dialysate outlet 22. A separate pump 41 or analogous device is provided on the line connected between the second balancing chamber 40 and the dialysate outlet 22 (or alternatively between the first balancing chamber 39 and the dialysate inlet 21) for removing liquid from the closed loop at a pre-set rate (UF mL/min). Thus, the dialysate flow rate through the dialysate outlet 22 is (x+UF mL/min). Further details on such a UF control mechanism are disclosed in U.S. Pat. No. 5,247,434, incorporated herein by reference.

While the present invention has been described in connection with preferred embodiments, it will be understood that it is not limited to those embodiments. On the contrary, the present invention is intended to cover all alternatives, modifications, and equivalents as may be included within the spirit and scope of the invention as defined by the appended claims.

What is claimed is:

1. A dialyzer comprising:

(a) a casing with a blood inlet, a blood outlet, a dialysate inlet, and a dialysate outlet;

(b) a hollow-fiber semipermeable membrane having a lumen, the fiber extending through the casing and being connected to the blood inlet and the blood outlet so as to conduct extracorporeal blood from the blood inlet through the lumen to the blood outlet while a dialysate flow is conducted from the dialysate inlet through the casing to the dialysate outlet, the dialysate flow exhibiting a pressure profile on the membrane from the dialysate inlet to the dialysate outlet; and (c) the dialyzer including an impediment serving to restrict dialysate flow through the casing in a first region compared to a second region adjacent the first region, the restriction to dialysate flow in the first region serving to increase dialysate pressure on the membrane in the first region compared to the second region sufficiently to cause the pressure profile through the casing from the dialysate inlet to the dialysate outlet to be non-linear.

2. The dialyzer as recited in claim 1 wherein the casing is substantially cylindrical.

3. The dialyzer as recited in claim 2 wherein the impediment comprises an external annular constriction of the casing between the first region and the second region.

4. The dialyzer as recited in claim 2 wherein the impediment comprises an internal annular restriction in the casing between the first region and the second region.

5. The dialyzer as recited in claim 4 wherein the internal annular restriction is positionally adjustable in the casing so as to allow a change in size of the first region relative to the second region to be made.

6. The dialyzer as recited in claim 2 wherein the impediment comprises an inclusion body located in the first region of the casing.

7. The dialyzer as recited in claim 2 wherein the impediment comprises a reduced size of the casing in the first region so as to provide the dialysate with a space having a reduced cross-sectional area through which to flow compared to the second region.

8. The dialyzer as recited in claim 1 adapted for use as a hemodiafilter.

9. The dialysate circuit comprising a dialyzer as recited in claim 1.

10. A dialyzer comprising:

(a) a casing;

(b) a bundle of hollow-fiber semipermeable membranes disposed in the casing, each hollow-fiber membrane having a lumen;

(c) a first inlet and a first outlet attached to the casing, the first inlet and outlet being connected to the fibers so as to conduct a first liquid in parallel through the lumina of the hollow-fiber membranes from the first inlet to the first outlet;

(d) a second inlet and a second outlet attached to the casing so as to conduct a second liquid though the casing from the second inlet to the second outlet, the second liquid exhibiting a pressure profile on the membranes during conduction of the second liquid from the second inlet to the second outlet; and (e) flow-restricting means situated between the second inlet and the second outlet for imparting a restriction to flow of the second liquid through the casing sufficiently to cause the pressure profile to be non-linear from the second inlet to the second outlet.

11. The dialyzer as recited in claim 10 further comprising a partition in the casing between a first portion of the bundle and a second portion of the bundle, said flow-restriction means comprising an opening through the partition for passage therethrough of the second liquid as the second liquid passes to the second portion of the bundle after contacting the first portion of the bundle.

12. The dialyzer as recited in claim 11 adapted for use as a hemodiafilter.

13. The dialysate circuit comprising a dialyzer as recited in claim 9.

14. A dialyzer comprising:

(a) a casing defining a dialyzer volume, and including a partition dividing the dialyzer volume into first and second portions, the partition defining at least one opening allowing liquid to flow therethrough from the first portion to the second portion;

(b) first and second groups of hollow-fiber semipermeable membranes, the first group extending through the first portion and the second group extending through the second portion, each of the fibers of each said group having a lumen;

(c) a blood inlet and a blood outlet attached to the casing so as to conduct extracorporeal blood from the blood inlet to the blood outlet through the lumina of the fibers of the first and second group;

(d) a dialysate inlet and a dialysate outlet attached to the casing so as to conduct dialysate from the dialysate inlet to the first portion, through the opening to the second portion, then to the dialysate outlet, the dialysate exhibiting a pressure profile on the membranes as the dialysate is conducted from the dialysate inlet to the dialysate outlet; and (e) the opening serving to restrict dialysate flow therethrough from the first portion to the second portion so as to increase dialysate pressure in the first region compared to the second region sufficiently to cause the pressure profile to be non-linear from the dialysate inlet to the dialysate outlet.

15. The dialyzer as recited in claim 14 adapted for use as a hemodiafilter.

16. The dialysate circuit comprising a dialyzer as recited in claim 14.

17. A dialyzer, comprising;

(a) a casing defining a dialysate compartment and having a blood inlet and a blood outlet, the dialysate compartment being operable to conduct dialysate entering the dialysate compartment;

(b) a semipermeable membrane configured as plural hollow fibers each having a lumen, the hollow fibers extending through the dialysate compartment so as to be operable to conduct extracorporeal blood through the lumina of the hollow fibers from the blood inlet to the blood outlet;

(c) the dialysate compartment having a first region and a second region, the first and second regions having a pressure barrier therebetween that is operable to cause, as dialysate enters the dialysate compartment, the first region to exhibit a pressure profile that is different from a pressure profile exhibited by the second region.

18. The dialyzer of claim 17, wherein the pressure profile in the first region is non-linear with the pressure profile in the second region.

19. The dialyzer of claim 17, wherein the pressure barrier comprises a partition substantially separating the first region from the second region.

20. The dialyzer of claim 19, wherein the partition defines an aperture for passage of dialysate between the first and second regions.

21. The dialyzer of claim 17, wherein the pressure barrier comprises a restriction in the casing between the first and second regions.

22. A dialyzer comprising:

(a) a casing with a blood inlet, a blood outlet, a dialysate inlet and a dialysate outlet;

(b) first and second groups of hollow-fiber semipermeable membranes, the first group representing a first region in the casing and the second group representing a second region in the casing, each of the fibers of the first and second groups having a lumen, the first and second groups connected to the blood inlet and the blood outlet so as to conduct extracorporeal blood from the blood inlet through the lumina of the fibers of the first and second groups to the blood outlet while dialysate is conducted though the casing, the dialysate flow exhibiting a pressure profile on the first and second groups from the first region to the second region; and (c) the dialyzer including a pressure barrier between the first region and the second region, the pressure barrier serving to restrict dialysate flow through the casing in the first region compared to the second region, the restriction to dialysate flow in the first region serving to increase dialysate pressure on the membrane in the first region compared to the second region sufficiently to cause the pressure profile through the casing from the dialysate inlet to the dialysate outlet to be non-linear.

23. The dialyzer as recited in claim 22 wherein the pressure barrier is operable, whenever dialysate is being conducted through the casing, to create a pressure profile in the first region that is different from the pressure profile in the second region.

* * * * *

UNITED STATES PATENT AND TRADEMARK OFFICE
CERTIFICATE OF CORRECTION

PATENT NO.  : 5,730,712
DATED       : March 24, 1998
INVENTOR(S) : Falkvall, et. al.

It is certified that error appears in the above-identified patent and that said Letters Patent is hereby corrected as shown below:

On the Cover Page:

Item [56], References Cited, U.S. Patent Documents, the following documents should be inserted:

|  |  |  |
|---|---|---|
| --4,148,606 | 4/1979 | Morita et al. |
| 4,201,673 | 5/1980 | Kanno et al. |
| 4,237,013 | 12/1980 | Yamazaki et al.-- |

Column 1, line 43, "dialyzero" should be -- dialyzer, --.

Column 6, line 56, --FIG.-9-- should be inserted after "the" and before "embodiment".

Column 7, line 34, "i.e." should be --I.e.--.

Column 9, line 29, "F" should be -- *l* --.

Column 13, line 56, the semi-colon ";" should be a colon --:--.

Signed and Sealed this

Fifteenth Day of December, 1998

*Attest:*

BRUCE LEHMAN

*Attesting Officer*    *Commissioner of Patents and Trademarks*